United States Patent
Friedt et al.

(10) Patent No.: US 10,123,611 B2
(45) Date of Patent: Nov. 13, 2018

(54) CONTAINER FOR ORAL CARE TOOLS AND METHOD OF ASSEMBLY AND USE

(71) Applicant: Ranir, LLC, Grand Rapids, MI (US)

(72) Inventors: Nicholas Friedt, Grand Rapids, MI (US); Kevin Kollar, Ada, MI (US)

(73) Assignee: Ranir, LLC, Grand Rapids, MI (US)

( * ) Notice: Subject to any disclaimer, the term of this patent is extended or adjusted under 35 U.S.C. 154(b) by 0 days.

(21) Appl. No.: 15/231,225

(22) Filed: Aug. 8, 2016

(65) Prior Publication Data
US 2018/0035798 A1    Feb. 8, 2018

(51) Int. Cl.
| | | |
|---|---|---|
| *A46B 15/00* | (2006.01) | |
| *B65D 43/16* | (2006.01) | |
| *A46B 9/04* | (2006.01) | |
| *A61C 15/04* | (2006.01) | |
| *A61C 15/02* | (2006.01) | |
| *A46B 17/00* | (2006.01) | |

(Continued)

(52) U.S. Cl.
CPC ............ *A46B 15/0091* (2013.01); *A46B 9/04* (2013.01); *A46B 15/0093* (2013.01); *A46B 15/0095* (2013.01); *A46B 17/00* (2013.01); *A46B 17/04* (2013.01); *A47G 21/12* (2013.01); *A61C 15/02* (2013.01); *A61C 15/043* (2013.01); *A61C 15/046* (2013.01); *B65D 43/16* (2013.01); *A46B 2200/108* (2013.01)

(58) Field of Classification Search
CPC .................. A68B 15/0091; A68B 9/04; A68B 2200/108; A68B 15/0093; A68B 15/0095; A68B 17/00; A68B 17/04; A61C 15/046; A61C 15/02; A61C 15/043; B65D 43/16; A47G 21/12

USPC ............................ 206/369, 362.4, 63.5, 380
See application file for complete search history.

(56) References Cited

U.S. PATENT DOCUMENTS 2,477,194 A * 7/1949 Millard .................. A47G 21/12
 132/329
3,438,486 A * 4/1969 Pinkas .................... A61C 15/02
 132/321

(Continued)

FOREIGN PATENT DOCUMENTS

DE 1854879 U 4/1962
DE 102011102571 A1 11/2012

(Continued)

OTHER PUBLICATIONS

European Search Report for EP 17184765.0-1659, dated Dec. 1, 2017.

*Primary Examiner* — Chun Cheung
(74) *Attorney, Agent, or Firm* — Warner Norcross + Judd LLP

(57) ABSTRACT

A container for storing a set of oral care tools in which multiple oral care tools are removably connected to connecting portion. The container includes a first portion that defines a first cavity configured to receive and capture the connecting portion therein and a second portion including first and second side walls defining a second cavity in which the oral care tools are stored. At least one of the first or second side walls can be pivoted to an open position to allow a consumer to access and separate an oral care tool from the connecting portion while the connecting portion is retained within the first cavity.

15 Claims, 7 Drawing Sheets

(51) Int. Cl.
*A46B 17/04* (2006.01)
*A47G 21/12* (2006.01)

(56) References Cited

U.S. PATENT DOCUMENTS

| | | | | |
|---|---|---|---|---|
| 5,855,215 | A * | 1/1999 | Clarke | A61C 15/02 |
| | | | | 132/321 |
| 6,044,848 | A * | 4/2000 | Huang | A61C 15/02 |
| | | | | 132/321 |
| 7,066,349 | B2 | 6/2006 | Cohen | |
| 7,124,883 | B1 | 10/2006 | Thomas et al. | |
| 7,424,952 | B2 | 9/2008 | Antler | |
| 7,537,110 | B2 | 5/2009 | Kutsch et al. | |
| 7,584,843 | B2 | 9/2009 | Kutsch et al. | |
| 9,259,303 | B2 * | 2/2016 | Studney | B65D 83/02 |
| 9,763,761 | B2 * | 9/2017 | Studney | A61C 19/02 |
| 2003/0135945 | A1 * | 7/2003 | Nordstrom | A46B 17/04 |
| | | | | 15/168 |
| 2008/0029409 | A1 * | 2/2008 | Antler | A61C 15/00 |
| | | | | 206/63.5 |
| 2014/0224825 | A1 | 8/2014 | Studney | |

FOREIGN PATENT DOCUMENTS

| | | |
|---|---|---|
| DE | 102014105395 A1 | 10/2015 |
| ES | 1056659 U | 4/2004 |
| FR | 2591877 A1 | 6/1987 |
| JP | 2007209567 A | 8/2007 |
| WO | 03053819 | 7/2003 |
| WO | 3094823 | 11/2003 |
| WO | 2012159745 | 11/2012 |

\* cited by examiner

CONTAINER FOR ORAL CARE TOOLS AND METHOD OF ASSEMBLY AND USE

BACKGROUND OF THE INVENTION

The present invention relates to a container for use in storing and dispensing oral care tools, including, but not limited to, interdental cleaning tools, in addition to a method of assembling the container and the oral care tools.

Oral care tools can be used in the practice of oral or dental hygiene to care for parts of the mouth, such as the teeth, gums, and tongue, etc. Oral care tools can be used to prevent and/or treat conditions and diseases associated with the mouth, non-limiting examples of which include dental cavities, gingivitis, periodontal disease, tooth decay, and bad breath. For example, interdental cleaning tools, such as toothpicks and brushes, are well known and are believed to help remove plaque and prevent gum recession. Interdental cleaning tools typically include a handle, and a narrow, elongated portion extending from the handle for insertion between a user's teeth. Interdental cleaning tools are often sold to consumers in a container as individual tools or sets of multiple connected tools. Conventional containers which are simple and cost effective to manufacture and load with the interdental cleaning tools can be cumbersome for a consumer to use to extract a single tool for dental cleaning. In contrast, containers with features designed to improve the consumer experience can be costly and time consuming to manufacture and load with the interdental cleaning tools.

SUMMARY OF THE INVENTION

The present invention provides a container for storing oral care tools, including, but not limited to, interdental cleaning tools, which facilitates loading the container with the oral care tools and allows a consumer to easily remove an individual oral care tool from the container for use.

In one embodiment of the invention, the container is designed to store at least one set of oral care tools and includes a first portion and second portion. The set of oral care tools includes multiple oral care tools removably connected to a connecting portion. The first portion of the container defines a first cavity that is configured to receive the connecting portion. The second portion comprises a first side wall and a second side wall, wherein at least one of the first or second side walls is movable relative to the other of the first or second side wall between (a) a closed position in which the first and second side walls define a second cavity within which the oral care tools are stored and (b) an open position in which at least one of the first or second side walls is pivoted away from the other to provide access to the oral care tools stored in the second cavity. When the connecting portion is inserted into the first cavity, the oral care tools extend into the second cavity. At least one of the first or second side walls can be pivoted to the open position to provide to access the second cavity to separate an oral care tool from the connecting portion while the connecting portion is retained within the first cavity.

In another embodiment, a container for storing at least one oral care tool includes a frame, a first and second side wall defining a first cavity, and an end cap defining a second cavity. The frame includes opposing first and second sides connected at the ends thereof by opposing first and second ends. The first side wall is connected with the first side of the frame and the second side wall is connected with the second side of the frame. At least one of the first or second side walls is pivotably connected to the adjacent side of the frame by at least one side wall hinge and at least one of the first or second walls is movable between (a) a closed position in which the first and second side walls define the first cavity within which the oral care tools are stored and (b) an open position in which at least one of the first or second side walls is pivoted away from the other to provide access to the first cavity. The end cap includes at least a portion which is pivotably connected with a remaining portion of the end cap or a portion of the frame, the end cap moveable between (a) a closed position in which the end cap and the frame define a second cavity and (b) an open position in which the end cap is pivoted away from the frame to provide access to the second cavity.

In still another embodiment, a method of assembling at least one set of oral care tools within a container is disclosed, the at least one set of oral care tools including multiple oral care tools removably connected to a connecting portion. The method includes forming a container comprising: (1) a first portion defining a first cavity configured to receive the connecting portion, and (2) a second portion including a first side wall and a second side wall, wherein at least one of the first or second side walls is movable relative to the other of the first or second side walls between (a) a closed position in which the first and second side walls define a second cavity within which the oral care tools are stored and (b) an open position in which at least one of the first or second side walls is pivoted away from the other to provide access to the oral care tools stored in the second cavity. The method also includes inserting the connecting portion into the first cavity. When the connecting portion is received within the first cavity, the at least one set of oral care tools extends into the second cavity with the at least one set of oral care tools connected with the connecting portion in the first cavity through an opening provided between the first and second portions. The opening is configured to retain the connecting portion within the first cavity when an oral care tool in the second cavity is separated from the connecting portion.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and practiced or carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DESCRIPTION

I. Structure

The embodiments of the invention generally relate to a container for storing oral care tools, including, but not limited to, interdental cleaning tools, and in particular for storing at least one set of oral care tools including multiple tools removably connected together. A consumer can separate an individual tool from the set for use while the remaining tools remain within the container.

Figure 6:
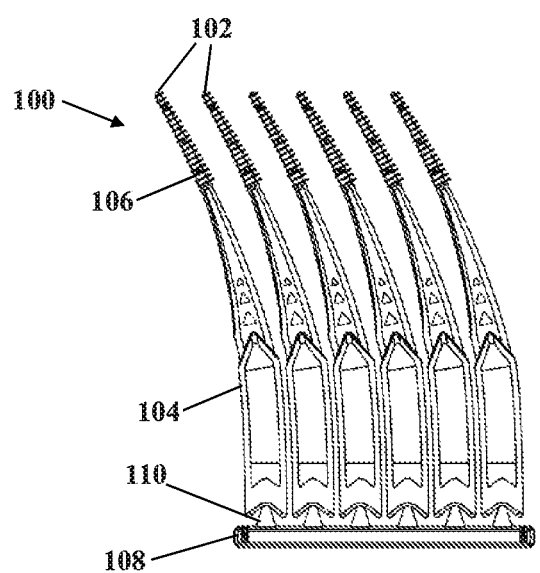
FIG. 6 is a side view of a set of oral care tools according to an embodiment of the invention.
Figure 7:
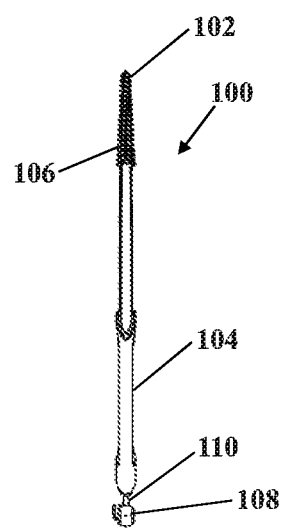
FIG. 7 is an end view of the set of oral care tools of FIG. 6.

FIGS. 1-4 illustrate a container 10 for storing at least one set of oral care tools 100 (FIGS. 6-7). While the embodiments of the container are discussed in the context of storing interdental cleaning tools, it will be understood that the container is not limited to storing interdental cleaning tools, but may be used in a similar manner to store other oral care products, non-limiting examples of which include flossing tools. As used herein, an interdental cleaning tool includes cleaners, picks, and/or brushes which can be used between adjacent teeth and around the teeth and gum area. The container 10 includes a first portion 12 defining a first cavity 14 that is at least partially connected with a second portion 16 which defines a second cavity 18. The first portion 12 can be fixedly connected with the second portion 16, integrally formed with the second portion 16, or at least partially separable from the second portion 16. The first portion 12, which is illustrated in the exemplary embodiment as an end cap, can include a bottom wall 20 and a plurality of end cap side walls 22*a-d* which together define the first cavity 14. The second portion 16 can include a first side wall 24 and a second side wall 26 which together form a clamshell-type container defining the second cavity 18.

Figure 5:
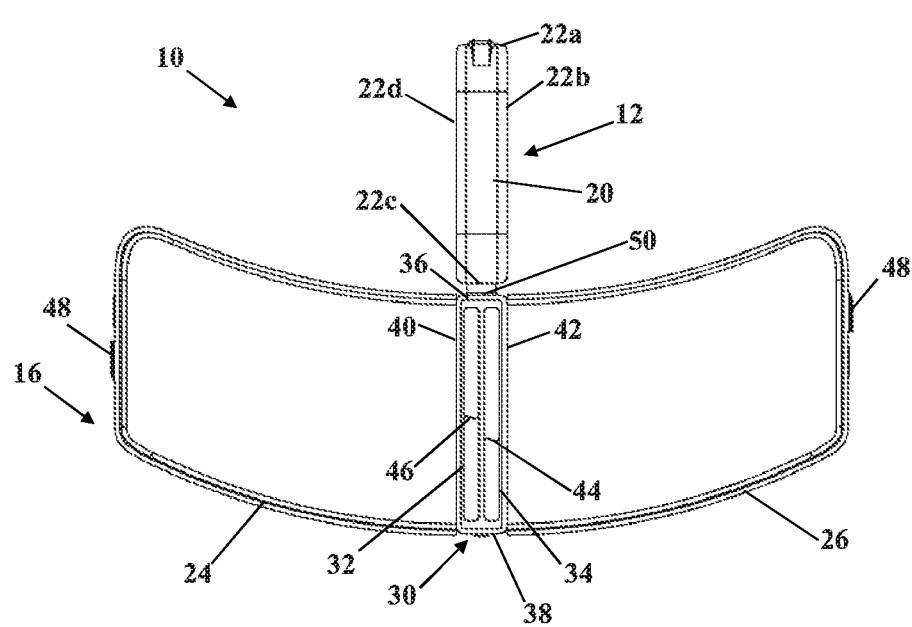
FIG. 5 is a top-down view of a container for storing oral care tools in an open condition.

Referring now to FIG. 5, the second portion 16 can include a frame 30 having first and second opposing sides 32, 34 connected by first and second ends 36, 38. The first and second side walls 24, 26 can be movably connected with first and second sides 32, 34, respectively, through one or more hinges 40, 42. In this manner, at least one of the first or second walls 24, 26 can be selectively pivoted from the closed position illustrated in FIGS. 1-2 to the open position illustrated in FIG. 5 to provide access to the second cavity 18. The hinges 40, 42 can be in the form of a living hinge including a thinned, cut, or scored hinge line that allows the side walls 24, 26 to pivot about the hinges 40, 42. Optionally, alternative hinge designs, such as a separate hinge can also be used.

In the embodiment illustrated in FIG. 5, both the first and second side walls 24, 26 are moveably connected with the respective first and second sides 32, 34 of the frame 30 such that one or both of the first and/or second side walls 24, 26 can be pivoted to an open position to provide access to the contents of the second cavity 18. Optionally, only one of the first or second side walls 24, 26 can be moveably connected with the frame 30 such that only one of the side walls 24, 26 is pivotable away from the other to provide access to the second cavity 18.

The frame 30 can also include two openings 44, 46 extending generally adjacent the first and second sides 32, 34 through which items can be pass between the first cavity 14 and the second cavity 18, as discussed in more detail below. Optionally, the frame 30 can include fewer or greater openings based on the number of interdental cleaning tool sets the container 10 is intended to hold.

The second portion 16 can also include a first portion locking mechanism 48 to facilitate maintaining the first and second side walls 24, 26 in the closed position. The first portion locking mechanism 48 can include any suitable mechanical lock or latch, the details of which are not germane to a complete understanding of the embodiments of the invention. Non-limiting examples of a first portion locking mechanism 48 include one or more snap-fit latches (as illustrated), a tongue-and-groove type fit between the first and second side walls 24, 26, an interference fit between the first and second side walls 24, 26, and a male-female style lock.

Still referring to FIG. 5, optionally, at least a portion of the first portion 12 can be moveable with respect to the second portion 16 to selectively provide access to the first cavity 14. For example, as illustrated in FIG. 5, the first portion 12 can be connected with the second portion 16 by a hinge 50 connecting the side wall 22*c* to the frame end 36. The first portion 12 can be pivoted about the hinge 50 between the closed position illustrated in FIG. 1 to the open position illustrated in FIG. 5 to selectively provide access to the first cavity 14. Alternatively, one or more hinges 50 can be provided on the side walls 22*b-d* to pivotably connect the first portion 12 with the second portion 16. In another example, only a portion of the first portion 12, such as the bottom wall 20, can be movable with respect to the second portion 16 to provide access to the first cavity 14. In this example, the first portion 12 can be fixedly connected to or integrally formed with the second portion 16. In still another example, the first portion 12 can optionally be entirely separable from the second portion 16 and connected to the second portion 16 through an interference or snap-fit connection.

Figure 1:
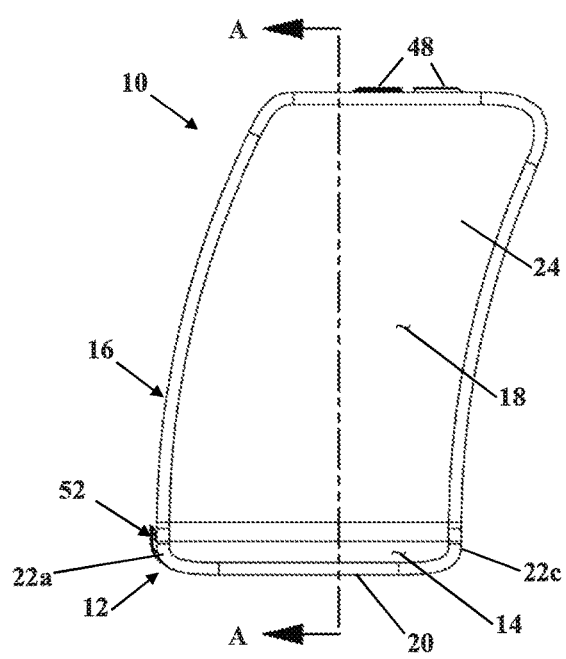
FIG. 1 is a side view of a container for storing oral care tools according to one embodiment of the invention.
Figure 2:
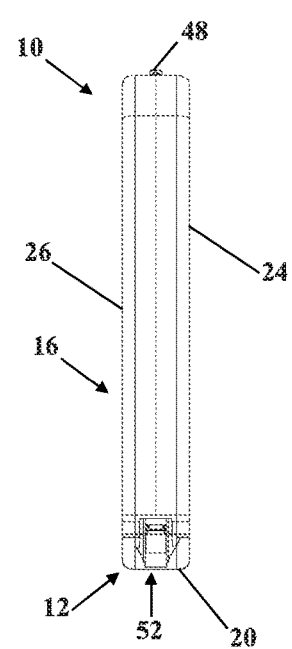
FIG. 2 is an end view of the container of FIG. 1.
Figure 3:
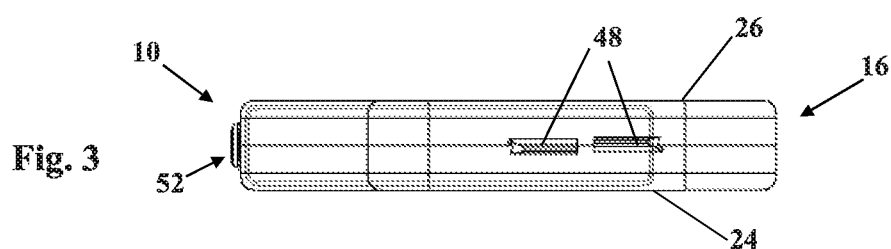
FIG. 3 is a top view of the container of FIG. 1.
Figure 4:
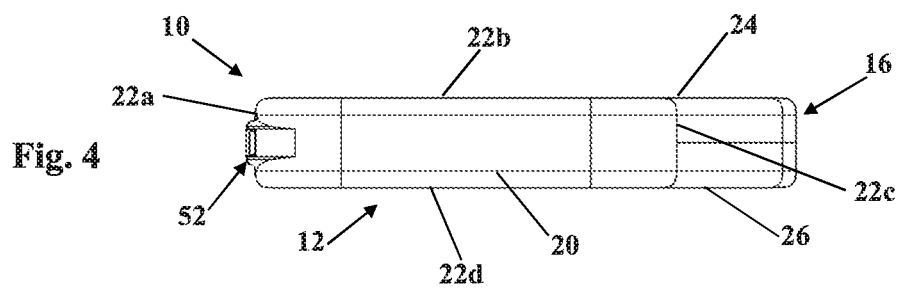
FIG. 4 is a bottom view of the container of FIG. 1.

A second portion locking mechanism 52, such as a latch, can be provided to releasably maintain the first portion 12 in the closed position illustrated in FIG. 1. As described above with respect to the first portion locking mechanism 48, the second portion locking mechanism 52 can be any suitable type of mechanism known in the art. In one example, the second portion locking mechanism 52 can be configured to selectively release the first portion 12, such that the first portion 12 can be re-opened and re-closed. In another example, the second portion locking mechanism 52 can be configured as a one-time locking mechanism in which the first portion 12 is intended to remain closed once it has been moved into the closed position illustrated in FIG. 1. In this example, the first portion 12 can be configured to remain closed under normal use conditions, although it will be understood that a motivated consumer could apply unusual deformation forces and/or tools in order to force the first portion 12 to re-open. The hinge 50 can be in the form of a living hinge including a thinned, cut, or scored hinge line that allows the first portion 12, or the moveable portion of the first portion 12, to pivot about the hinge line. The hinge 50 can be the same or different than the hinges 40, 42, and can optionally include alternative hinge designs, such as a separate hinge.

Referring again to FIG. 5, the frame 30 is illustrated as being integrally formed with the second portion 16, however, it is within the scope of the invention for the frame 30 to be integrally formed with the first portion 12 or to be a separate component connected with one or both of the first or second portions 12, 16. For example, when the first portion 12 is not moveable with respect to the second portion 16, and does not include a moveable portion, the frame 30 can be integrally formed with the first portion 12 such that the first and second side walls 24, 26 are connected directly with the first portion 12. In this example, there may or may not be any visual distinction between the frame 30 and the first portion 12. In another example, the first and second side walls 24, 26 can be connected directly with the first portion 12 and the frame 30 can be a separate component that is connected with either or both the first portion 12 and/or the second portion 16.

FIGS. 6-7 illustrate an exemplary set 100 of interdental cleaning tools 102 that can be used with the container 10 of FIGS. 1-5. The interdental cleaning tools 102 can include a handle portion 104 and a cleaning portion 106. The cleaning portion 106 can be in the form of a pick or include any combination of brushes, bristles, or nubs to facilitate interdental cleaning. Each of the interdental cleaning tools 102 can be connected with a connecting portion 108, such as a runner, by a bridge element 110. The bridge element 110 can be connected with the handle portion 104 of the interdental cleaning tool 102 by a frangible connection such that the consumer can selectively remove the interdental cleaning tool 102 from the set 100 for use by breaking the frangible connection between the handle portion 104 and the bridge element 110. Optionally, the frangible connection can be located between the bridge element 110 and the runner 108 such that the bridge element 110 remains connected with the handle portion 104 when it is separate from the runner 108.

Figure 8:
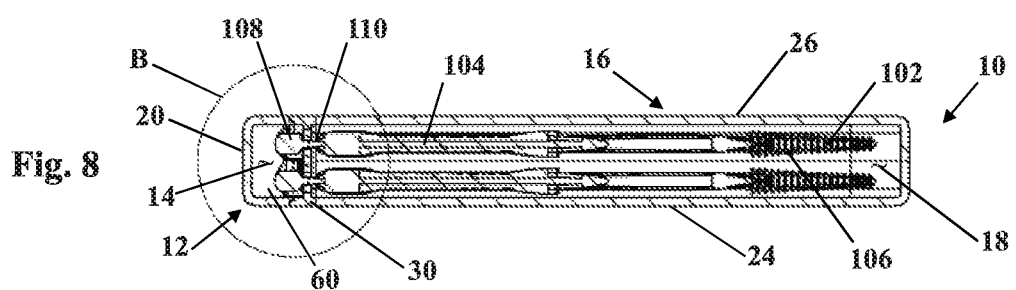
FIG. 8 is a cross-sectional view taken along the line A-A in FIG. 1.
Figure 9:
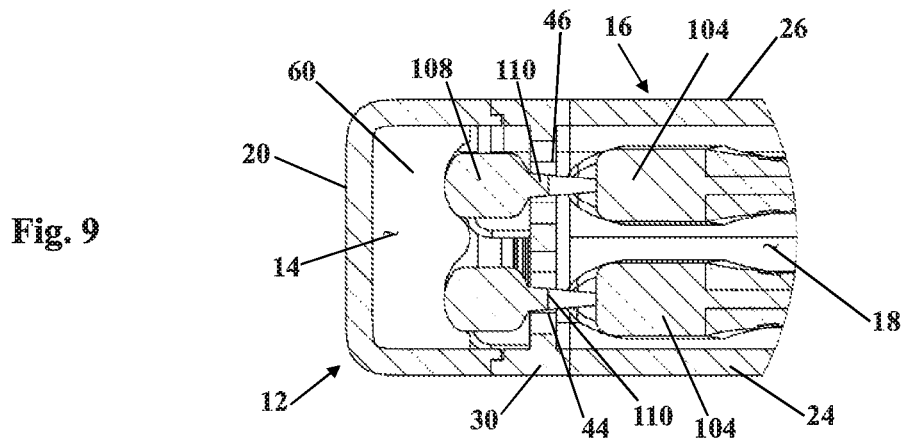
FIG. 9 is an enlarged view of the circled portion in FIG. 8.

Referring now to FIGS. 8 and 9, the interdental cleaning tool set 100 has dimensions so as to be stored within the container 10. The runner 108 is configured to be received within the first cavity 14, while the interdental cleaning tools 102 are configured to be received with the second cavity 18. The bridge elements 110 can be configured to connect the interdental cleaning tools 102 in the second cavity 18 with the runner 108 in the first cavity 14 through the openings 44, 46 in the frame 30.

The first portion 12 can be provided with an optional runner support 60 to maintain the runner 108 in a desired position within the first cavity 14 and to provide support and/or stability to the interdental cleaning tool set 100. For example, the runner support 60 can be configured to support the runner 108 such that the runner 108 is grasped between the frame 30 and the runner support 60 to minimize movement of the runner 108. In another example, the runner support 60 can be configured to support the runner 108 such that a bottom of the handle portion 104 abuts the frame 30. In another example, the runner support 60 can be configured to support the runner 108 such that the frangible connection between the handle portion 104 and the bridge element 110 is generally aligned with the frame 30 to facilitate separating the interdental cleaning tool 102 from the bridge element 110. The runner support 60 can optionally stabilize the interdental cleaning tool set 100 within the container 10 to facilitate separating an individual cleaning tool 102 from the set 100. In another example, the first portion 12 does not include the optional runner support 60 and the first portion 12 is configured such that the bottom wall 20 of the first portion 12 supports the runner 108 in the desired position within the first cavity 14. As discussed above, the frame 30, and thus the optional runner support 60, can be configured to support any number of interdental cleaning tool sets 100.

II. Method of Assembly and Use

Figure 10:
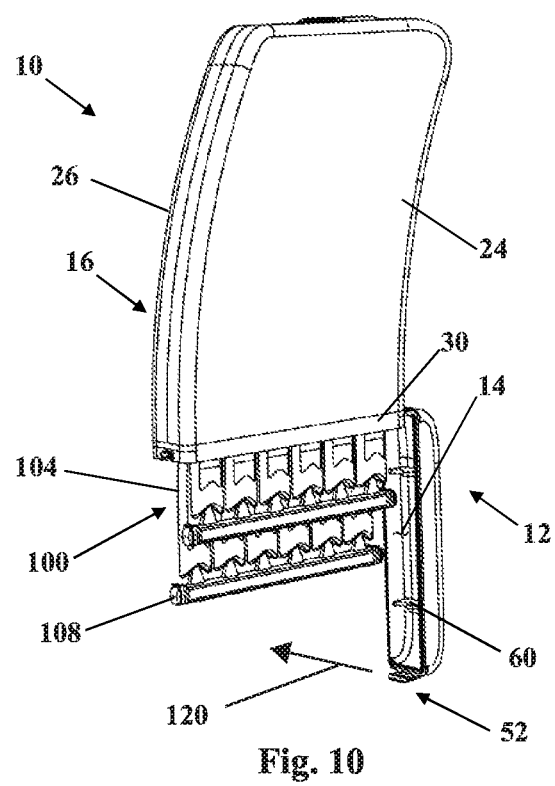
FIG. 10 illustrates a method of loading a set of oral care tools into a container according to an embodiment of the invention.

FIG. 10 illustrates a manner in which the container 10 can be loaded with one or more interdental cleaning tool sets 100. The container 10 can be loaded at a manufacturing facility as a single use container and/or optionally re-loaded and re-used by the consumer. The container 10 can be loaded with the interdental cleaning tool sets 100 with the first portion 12 pivoted about its hinge 50 into the open position illustrated in FIG. 10. The cleaning portion 106 of each tool set 100 can be inserted into the second cavity 18 of the second portion 16 through the first and second openings 44, 46 in the frame 30. Once the interdental cleaning tool 102 is positioned within the second cavity 18, the first portion 12 can be pivoted about the hinge 50, as illustrated by arrow 120, into the closed position illustrated in FIG. 11. In one example, the container 10 can be configured such that once the runner 108 is captured within the first cavity 14, the first portion 12 can be selectively opened and re-closed, such that the container 10 can be reused. In another example, the container 10 can be configured as a single use container in which the first portion 12 is not designed to be selectively opened and re-closed following the initial closing of the first portion 12 and capturing of the runner 108.

The first and second openings 44, 46, the interdental cleaning tools 102, and optionally the bridge element 110 can have dimensions such that the interdental cleaning tools 102 and optionally at least a portion of the bridge element 110 can pass through the first and second openings 44, 46 during loading of the container 10. The first cavity 14 and the runner 108 are each configured such that the runner 108 fits within the first cavity 14. The dimensions of the runner 108 and the first and second openings 44, 46 are also configured so as to inhibit the runner 108 from passing from the first cavity 14 through the first and second openings 44, 46 into the second cavity 18. In this manner, the runner 108 can be captured and retained within the first cavity 14 defined by the first portion 12 and the frame 30. For example, at least one of a width and/or length of the runner 108 can be greater than the corresponding width and/or length of the first and second openings 44, 46 to inhibit the runner 108 from passing through the first and second openings 44, 46.

Figure 11:
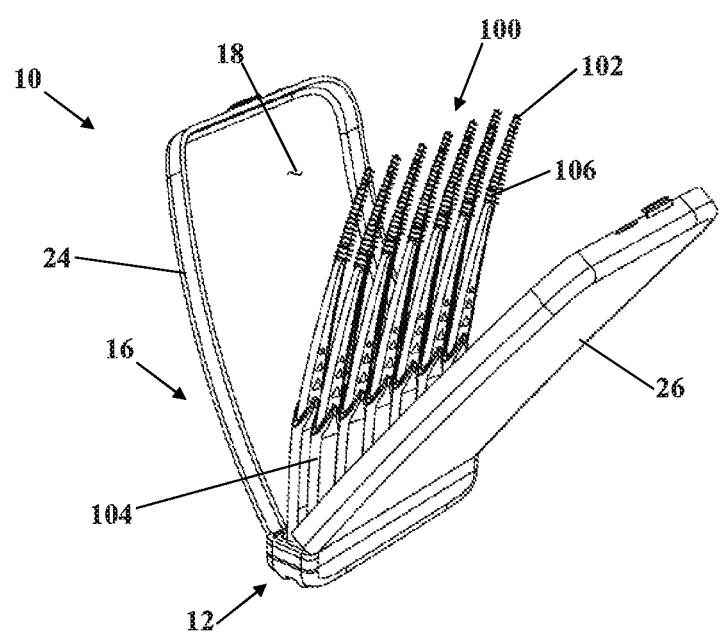
FIG. 11 illustrates a method of removing an individual oral care tool from a container according to an embodiment of the invention.

Referring now to FIG. 11, to extract an interdental cleaning tool 102 from the container 10, the consumer can pivot one or both of the first and second side walls 24, 26 about their respective hinges 40, 42 to gain access to the tools 102 stored within the second cavity 18. A consumer can grasp one or more of the interdental cleaning tools 102 and bend and/or pull the tool 102 to break the frangible connection between the tool handle 104 and the bridge element 110. As described above, the runner 108 is captured within the first cavity 14 such that the consumer can remove an individual interdental cleaning tool 102 from the set 100 without removing the whole set 100 from the container 10. At least one of a length and/or width of the runner 108 and the first and second openings 44, 46 can be configured such that it is difficult or impossible for the runner 108 to be pulled through either of the first and second openings 44, 46 into the second cavity 18 when a consumer removes an individual interdental cleaning tool 102 from the set 100. The first and/or second side walls 24, 26 can then be pivoted back into the closed position illustrated in FIG. 10 to store the remaining interdental cleaning tools 102 for future use.

In another example, rather than providing a pivotable first portion 12 which remains at least partially attached to the second portion 16, the first portion 12 can be a separate piece that is connected with second portion 16 following loading of the interdental cleaning tools 102. In this example, the first portion 12 can be connected with the second portion 16 through a snap or interference-type fit to capture and retain the runner 108 within the first cavity 14 in the same manner as described above with respect to FIG. 10.

In another example, the first and second openings 44, 46 in the frame 30 can be configured to flex to allow the runner 108 to be passed through the first and second openings 44, 46 and inserted into the first cavity 14 through a snap-fit type mechanism. Once the runner 108 passes through the first and second openings 44, 46, the portions of the frame 30 defining the openings 44, 46 can return to their original position, thus capturing the runner 108 within the first cavity 14. At least one of a length and/or width of the runner 108 and the first and second openings 44, 46 in their unflexed, original position can be configured such that it is difficult or impossible for the runner 108 to be pulled through either of the first and second openings 44, 46 into the second cavity 18 when a consumer removes an individual interdental cleaning tool 102 from the set 100. In this example, the runner 108 can be inserted into the first cavity 14 without separating the first portion 12 from the second portion 16 and without having to insert the interdental cleaning tools 102 in through the bottom of the container 10, and thus the first portion 12 would not need to be moveable with respect to the second portion 16 or include a moveable portion. Instead, the first portion 12 could optionally be integrally formed with the second portion 16. The consumer can then operate the container 10 in the same manner as described above with respect to FIG. 11 to remove an interdental cleaning tool 102 for use. In this example, the interdental cleaning tools 102 would not need to be configured to fit through the first and second openings 44, 46 because the interdental cleaning tools 102 are not being loaded by passing from the first cavity 14 through the first and second openings 44, 46 into the second cavity 18.

The embodiments of the container 10 described herein can be used to provide a container that is easy to load with interdental cleaning tools during manufacturing and optional re-use, and also is easy for a consumer to use to remove an individual interdental cleaning tool from the container for use.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit of the invention and broader aspects of the invention as defined in the appended claims, which are to be interpreted in accordance with the principles of patent law, including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A container for storing at least one set of oral care tools, the at least one set of oral care tools including multiple oral care tools removably connected to a connecting portion, the container comprising:
   a first portion defining a first cavity configured to receive the connecting portion; and
   a second portion comprising a first side wall and a second side wall, wherein at least one of the first or second side walls is movable relative to the other of the first or second side wall between (a) a closed position in which the first and second side walls define a second cavity within which the oral care tools are stored and (b) an open position in which at least one of the first or second side walls is pivoted away from the other to provide access to the oral care tools stored in the second cavity,
   wherein when the connecting portion is inserted into the first cavity, the oral care tools extend into the second cavity, and wherein at least one of the first or second side walls can be pivoted to the open position to provide access to the second cavity to separate an oral care tool from the connecting portion while the connecting portion is retained within the first cavity
   further comprising at least one opening between the first portion and the second portion configured to retain the connecting portion within the first cavity.

2. The container of claim 1 wherein the at least one opening is defined by a frame having opposing first and second sides connected by first and second ends, and wherein the first side wall is connected with the first side and the second side wall is connected with the second side, at least one of the first or second side walls pivotably connected with the adjacent first or second side by at least one hinge.

3. The container of claim 2 wherein the frame is one of integrally formed with the first portion, integrally formed with the second portion, or a separate component connected with one or both of the first or second portions.

4. The container of claim 1 wherein the opening is configured to resiliently flex to allow the connecting portion to be inserted through the opening into the first cavity through a snap-fit connection.

5. The container of claim 1 wherein at least a portion of the first portion is at least partially separable from the second portion to allow the connecting portion to be inserted into the first cavity.

6. The container of claim 5 wherein the first portion is pivotably connected with the second portion, and wherein the first portion can be pivoted away from the second portion to an open position to allow the connecting portion to be inserted into the first cavity and pivoted into a closed position to capture the connecting portion between the first portion and the second portion.

7. The container of claim 1 wherein when the connecting portion is received within the first cavity, the oral care tools stored in the second cavity are connected with the connecting portion through the opening.

8. The container of claim 1 wherein the first portion includes two openings and the first cavity is configured to retain a first connecting portion of a first set of oral care tools and a second connecting portion of a second set of oral care tools.

9. A container for storing at least one oral care tool, the container comprising:
   a frame having opposing first and second sides connected at the ends thereof by opposing first and second ends;
   a first side wall connected with the first side of the frame and a second side wall connected with the second side of the frame, wherein at least one of the first or second side walls is pivotably connected to the adjacent side of the frame by at least one side wall hinge and where at least one of the first or second walls is movable between (a) a closed position in which the first and second side walls define a first cavity within which the oral care tools are stored and (b) an open position in which at least one of the first or second side walls is pivoted away from the other to provide access to the first cavity; and
   an end cap, at least a portion of which is pivotably connected with a remaining portion of the end cap or a portion of the frame, the end cap moveable between (a) a closed position in which the end cap and the frame define a second cavity and (b) an open position in which the end cap is pivoted away from the frame to provide access to the second cavity.

10. The container of claim 9 wherein the first side wall is pivotably connected with the first side of the frame and the second side wall is pivotably connected with the second side of the frame.

11. The container of claim 9 wherein the frame includes at least one opening between the first and second sides.

12. The container of claim 11 wherein when the end cap or the pivotable portion of the end cap is pivoted to the open position, the at least one oral care tool can be inserted into the first cavity by passing through the second cavity and the at least one opening in the frame.

13. The container of claim 12 wherein the at least one oral care tool is connected with a connecting portion, and wherein the at least one opening is configured to retain the connecting portion within the second cavity and allow the oral care tool to pass through to the first cavity.

14. The container of claim 9 wherein the frame is one of integrally formed with the end cap, integrally formed with the first and second side walls, or a separate component connected with one or both of the end cap or the first and second side walls.

15. A container for storing at least one set of oral care tools, the at least one set of oral care tools including multiple oral care tools removably connected to a connecting portion, the container comprising:
   a first container portion defining a first cavity; and
   a second container portion connected to the first container portion by at least one opening, the second container portion comprising a first side wall and a second side wall, wherein at least one of the first or second side walls is movable relative to the other of the first or second side wall between (a) a closed position in which the first and second side walls define a second cavity and (b) an open position in which at least one of the first or second side walls is pivoted away from the other to provide access to the second cavity;
   wherein the connecting portion is retained within the first cavity when the connecting portion is inserted into the first cavity, and wherein when the connecting portion is inserted into the first cavity, the oral care tools extend through the at least one opening into the second cavity, and wherein at least one of the first or second side walls can be pivoted to the open position to provide access to the second cavity to separate an oral care tool from the connecting portion while the connecting portion is retained within the first cavity.

* * * * *